US012599779B2

(12) United States Patent
Savage et al.

(10) Patent No.: US 12,599,779 B2
(45) Date of Patent: Apr. 14, 2026

(54) LIGHT THERAPY APPARATUSES

(71) Applicant: Photopharmics, Inc., Highland, UT (US)

(72) Inventors: Kent W. Savage, Highland, UT (US); Daniel N. Adams, American Fork, UT (US); Gregory Lynn Willis, Woodend (AU)

(73) Assignee: PhotoPharmics, Inc., Lehi, UT (US)

( * ) Notice: Subject to any disclaimer, the term of this patent is extended or adjusted under 35 U.S.C. 154(b) by 2030 days.

(21) Appl. No.: 14/094,312

(22) Filed: Dec. 2, 2013

(65) Prior Publication Data

US 2014/0088439 A1 Mar. 27, 2014

Related U.S. Application Data

(63) Continuation-in-part of application No. PCT/US2012/068045, filed on Dec. 5, 2012, which is
(Continued)

(51) Int. Cl.
*A61N 5/06* (2006.01)
*A61B 5/00* (2006.01)

(52) U.S. Cl.
CPC .......... *A61N 5/0613* (2013.01); *A61B 5/0059* (2013.01); *A61N 5/0622* (2013.01); *A61N 2005/0663* (2013.01)

(58) Field of Classification Search
CPC ................ A61N 5/0613; A61N 5/0622; A61N 2005/0663; A61N 2005/0667;
(Continued)

(56) References Cited

U.S. PATENT DOCUMENTS 4,858,609 A * 8/1989 Cole ..................... A61M 21/00
607/91
5,265,598 A 11/1993 Searfoss et al.
(Continued)

FOREIGN PATENT DOCUMENTS

AU 2008271911 A1 8/2009
AU 2012262123 B2 8/2015
(Continued)

OTHER PUBLICATIONS

European Patent Office, "Supplementary European Search Report," mailed Mar. 24, 2015 in European patent application No. 12793321. 6.
(Continued)

*Primary Examiner* — Niketa Patel
*Assistant Examiner* — Sebastian X Lukjan
(74) *Attorney, Agent, or Firm* — DENTONS Durham Jones Pinegar

(57) ABSTRACT

Light therapy apparatuses are configured to expose a subject to light that is tailored to address and/or diagnose at least one motor-related neurological condition. Blue-green light and green light are useful for treating motor-related neurological conditions or their symptoms. Deep red light and near infrared radiation may facilitate the repair of retinal cells and/or neurons that may be responsible for motor-related neurological conditions. Amber, orange and red light enable the early diagnosis of motor-related neurological conditions.

21 Claims, 2 Drawing Sheets

Related U.S. Application Data a continuation-in-part of application No. PCT/US2012/040284, filed on May 31, 2012, application No. 14/094,312 is a continuation-in-part of application No. PCT/US2012/040284, filed on May 31, 2012.

(60) Provisional application No. 61/491,864, filed on May 31, 2011.

(58) Field of Classification Search
CPC .... A61N 2005/0648; A61N 2005/0659; A61B 5/0059; A61B 5/4082; A61B 5/4836
USPC .......................................................... 607/88
See application file for complete search history.

(56) References Cited

U.S. PATENT DOCUMENTS

| | | | |
|---|---|---|---|
| 5,304,212 | A | 4/1994 | Czeisler et al. |
| 6,218,366 | B1 | 4/2001 | St. Cyr et al. |
| 6,350,275 | B1 | 2/2002 | Vreman et al. |
| 8,556,951 | B2 | 10/2013 | Witt et al. |
| 11,191,478 | B2 * | 12/2021 | Willis ................... A61B 5/4839 |
| 2001/0056296 | A1 | 12/2001 | Sugita et al. |
| 2004/0158300 | A1 | 8/2004 | Gardiner |
| 2004/0225340 | A1 | 11/2004 | Evans |
| 2005/0024853 | A1 * | 2/2005 | Thomas-Benedict ........................ A61N 5/0619 362/103 |
| 2005/0237479 | A1 | 10/2005 | Rose |
| 2006/0106436 | A1 | 5/2006 | Medes et al. |
| 2008/0051858 | A1 | 2/2008 | Haber et al. |
| 2008/0077199 | A1 | 3/2008 | Shefi et al. |
| 2008/0091250 | A1 * | 4/2008 | Powell ................... A61M 21/00 607/90 |
| 2008/0103561 | A1 * | 5/2008 | Moscovici ........... A61N 5/0618 607/88 |
| 2008/0141296 | A1 | 6/2008 | Yoon |
| 2009/0204186 | A1 * | 8/2009 | Gruber ................... G02C 5/001 607/88 |
| 2010/0189698 | A1 | 7/2010 | Willis |
| 2010/0217358 | A1 | 8/2010 | Herbert et al. |
| 2010/0331928 | A1 | 12/2010 | Dunning et al. |
| 2011/0144410 | A1 | 6/2011 | Kennedy |
| 2011/0251657 | A1 | 10/2011 | Miyake et al. |

FOREIGN PATENT DOCUMENTS

| | | | |
|---|---|---|---|
| CN | 101031320 | A | 9/2007 |
| CN | 101687101 | A | 3/2010 |
| CN | 101888875 | A | 11/2010 |
| CN | 102000378 | A | 4/2011 |
| CN | 102448372 | A | 5/2012 |
| CN | 103687647 | B | 3/2014 |
| EP | 2714195 | B1 | 7/2018 |
| JP | H044506 | A | 1/1992 |
| JP | H08190804 | A | 7/1996 |
| JP | 2002065875 | A | 3/2002 |
| JP | 2005063687 | A | 3/2005 |
| JP | 2005310654 | A | 11/2005 |
| JP | 2009112804 | A | 5/2009 |
| JP | 2010526645 | A | 8/2010 |
| JP | 2010531810 | A | 9/2010 |
| JP | 2011072388 | A | 4/2011 |
| JP | 6129959 | B2 | 5/2017 |
| KR | 20010112372 | A | 12/2001 |
| RU | 2142829 | C1 | 12/1999 |
| WO | 2000059504 | A1 | 10/2000 |
| WO | 2004096364 | A1 | 11/2004 |
| WO | 2008069103 | A1 | 6/2008 |
| WO | 2008141296 | A1 | 11/2008 |
| WO | 2009003226 | A1 | 1/2009 |
| WO | 2009/023968 | A1 | 2/2009 |
| WO | 2010039886 | A1 | 4/2010 |
| WO | 2010041717 | A1 | 4/2010 |
| WO | 2010122434 | A1 | 10/2010 |
| WO | 2011135362 | A2 | 11/2011 |
| WO | 2012166972 | A1 | 6/2012 |
| WO | 2012164393 | A1 | 12/2012 |
| WO | 2013179082 | A1 | 12/2013 |

OTHER PUBLICATIONS

IP Australia, "Patent Examination Report No. 1," mailed Sep. 26, 2014 in Australian patent application No. 2012262123.
United States Patent and Trademark Office Acting as the International Searching Authority, "International Search Report and Written Opinion," mailed Sep. 7, 2012, in corresponding PCT application No. PCT/US2012/040284.
United States Patent and Trademark Office Acting as the International Searching Authority, "International Search Report and Written Opinion," mailed Feb. 15, 2013, in corresponding PCT application No. PCT/US2012/068045.
https://en.wikipedia.org/wiki/Light_therapy, Accessed Mar. 9, 2020.
Brainard, GB, et al., "Action Spectrum for Melatonin Regulation in Humans: Evidence for a Novel Circadian Photoreceptor," J Neurosci, 21(16):6405-6412 (Aug. 15, 2001).
IP Australia, "Examination Report," Australian Patent Application No. 2012381077, Nov. 24, 2016.
IP Australia, "Examination Report," Australian Patent Application No. 2017265164, Feb. 5, 2019.
IP Australia, "Examination Report," Australian Patent Application No. 2015261684, Sep. 21, 2016.
Canadian Intellectual Property Office, "Second Examiner's Report," Canadian Patent Application No. 2837993, Mar. 25, 2019.
Canadian Intellectual Property Office, "Examiner's Report," Canadian Patent Application No. 2837993, Jan. 18, 2018.
State Intellectual Property Office, "First Office Action," Chinese Patent Application No. 201280034068.0, Jul. 14, 2015.
State Intellectual Property Office, "Second Office Action," Chinese Patent Application No. 201280034068.0, Apr. 5, 2016.
State Intellectual Property Office, "First Office Action," Chinese Patent Application No. 201280074570.4, May 5, 2016.
State Intellectual Property Office, "First Office Action," Chinese Patent Application No. 201610836119.1, Apr. 3, 2018.
China National Intellectual Property Administration, "Office Action," Chinese Patent Application No. 201811168241.1, Nov. 4, 2020.
State Intellectual Property Office, "Second Office Action," Chinese Patent Application No. 201280074570.4, Feb. 17, 2017.
State Intellectual Property Office, "Second Office Action," Chinese Patent Application No. 201610836119.1, Feb. 2, 2019.
State Intellectual Property Office, "Third Office Action," Chinese Patent Application No. 201280074570.4, Oct. 24, 2017.
European Patent Office, "Supplementary European Search Report," European Patent Application No. 12878034.3, Apr. 19, 2016.
European Patent Office, "Communication Pursuant ot Aticle 94(3) EPC," European Patent Application No. 12878034.3, Apr. 3, 2017.
Japan Patent Office, "Notice of Reasons for Rejection," Japanese Patent Application No. 2014513713, Apr. 1, 2016.
Japan Patent Office, "Notice of Reasons for Rejection," Japanese Patent Application No. 2015514978, Sep. 6, 2016.
Japan Patent Office, "Notice of Reasons for Rejection," Japanese Patent Application No. 2017078785, Feb. 8, 2018.
Japan Patent Office, "Notice of Reasons for Rejection," Japanese Patent Application No. 2018026670, Nov. 26, 2018.
Japan Patent Office, "Notice of Reasons for Rejection," Japanese Patent Application No. 2014513713, Jan. 5, 2017.
Japan Patent Office, "Notice for Allowance" Japanese Patent Application No. 2015514978, Feb. 13, 2017.
Japan Patent Office, "Notice of Reasons for Rejection," Japanese Patent Application No. 2018026670, Oct. 30, 2019.
Korean Intellectual Property Office, "Notice of Grounds for Rejection," Korean Patent Application No. 10-2014-7036936, Nov. 30, 2018.
Korean Intellectual Property Office, "Notice of Grounds for Rejection," Korean Patent Application No. 10-2014-7036936, Oct. 16, 2019.

(56)　　　　References Cited

OTHER PUBLICATIONS

Korean Intellectual Property Office, "Notice of Grounds for Rejection," Korean Patent Application No. 10-2013-7035022, Nov. 21, 2018.
Korean Intellectual Property Office, "Notice of Grounds for Rejection," Korean Patent Application No. 10-2013-7035074, Jul. 31, 2018.
Japan Patent Office, "First Office Action Appeal Board," Japanese Patent Application No. 2014513269, Sep. 18, 2018.
Korean Intellectual Property Office, "Decision for Grant of Patent," Korean Patent Application No. 10-2021-7012269, Jan. 13, 2022.
IP Australia, "Examination Report," Australian Patent Application No. 2017261574, Jan. 14, 2019.
Japan Patent Office, "Decision of Refusal," Japanese Patent Application No. 2014513713, Oct. 18, 2017.
Canadian Intellectual Property Office, "Examiner's Report," Canadian Patent Application No. 2874996, Jun. 26, 2018.
Canadian Intellectual Property Office, "Examiner's Report," Canadian Patent Application No. 2874996, Jun. 3, 2019.
Canadian Intellectual Property Office, "Commissioner's Notice—Application Found Allowable," Canadian Patent Application No. 2837993, Dec. 14, 2021.
Willis, G.L., "Parkinson's disease as a neuroendocrine disorder of circadian function: dopamine-melatonin imbalance and the visual system in the genesis and progression of the degenerative process," Reviews in the Neurosciences, 19:245-316 (2008).
Korean Intellectual Property Office, "Notice of Grounds for Rejection," Korean Patent Application No. 10-2020-7007340, Mar. 27, 2020.
China National Intellectual Property Administration, "Office Action," Chinese Patent Application No. 201811168241.1, Dec. 15, 2021.
Korean Intellectual Property Office, "Gourds for Rejection" Korean Patent Application No. 10-2021-7012269, May 12, 2021.
Japan Patent Office, "Notice of Reasons for Rejection," Japanese Patent Application No. 2018026670, Nov. 2, 2021.
Korean Intellectual Property Office, "Notice of Ruling to reject Amendment," Korean Patent Application No. 10-2020-7007340, Feb. 22, 2021.
Canadian Intellectual Property Office, "Examiner's Report," Canadian Patent Application No. 2837993, Feb. 17, 2021.
European Patent Office, "European Search Report," European Patent Application No. 12793321.6, Aug. 17, 2016.
European Patent Office, "Supplementary European Search Report," European Patent Application No. 12793321.6, Apr. 26, 2017.
European Patent Office, "Communication Under 71(3)," European Patent Application No. 12793321.6, Jan. 3, 2018.
Korean Intellectual Property Office, "Notice of Refusal," Korean Patent Application No. 2013-7035074, Jun. 26, 2019.

Canadian Intellectual Property Office, "Examination Search Report," Canadian Patent Application No. 2874996, Feb. 19, 2021.
Canadian Intellectual Property Office, "Examination Search Report," Canadian Patent Application No. 2874996, Jun. 3, 2019.
China National Intellectual Property Administration, "Fifth Office Action," Chinese Application No. 201811168241.1, Mar. 12, 2020.
Canadian Intellectual Property Office, "Commissioner's Notice—Application Found Allowable," Canadian Application No. 2,874,996, May 30, 2023.
Japan Patent Office, "Office Action," Japanese Application No. 2018-026670, Jun. 30, 2023.
Korean Intellectual Property Office, "Notice of Grounds for Rejection," Korean application No. KR10-2020-7007340, Mar. 27, 2020.
China National Intellectual Property Administration, "First Office Action," Chinese application No. CN201811168241.1, Mar. 12, 2020.
Canadian Intellectual Property Office, "Examiner's Report," Canadian application No. 2874996, May 20, 2020.
Giuliani, Alessandro et al., "Low infra red laser light irradiation on cultured neural cells: effects on mitochondria and cell viability after oxidative stress," BMC Complementary and Alternative Medicine 2009, 9(8): 1-10 (2009).
Canadian Intellectual Property Office, "Examiner's Report," Canadian application No. 2837993, Apr. 16, 2020.
Korean Intellectual Property Office, "Notice of Final Rejection," Korean application No. 10-2014-7036936, Apr. 29, 2020.
Japan Patent Office, "Grounds for Rejection," for Japanese application No. 2018-026670, Apr. 16, 2020.
Japan Patent Office, "Office Action," Japanese application No. 2018-026670, Nov. 2, 2021.
Japan Patent Office, "Office Action," Japanese application No. 2021-018295, Nov. 17, 2021.
Canadian Intellectual Property Office, "Examiner's Report," Canadian application No. 2874996, Dec. 1, 2021.
Japan Patent Office, "Reasons for Rejection," Japanese Patent Application No. 2018-026670, Feb. 27, 2025.
Japan Patent Office, "Decision for Rejection," Japanese Patent Application No. 2022-076149, Nov. 7, 2023.
Korean Intellectual Property Office, "Notice of Grounds for Rejection," Korean Patent Application No. 10-2024-7004222, Dec. 2, 2024.
Japan Patent Office, "Office Action," Japanese Application No. 2024-034923, May 12, 2025.
Korean Intellectual Property Office, "Notice of Final Rejection," Korean Application No. 10-2022-7012483, Sep. 6, 2023.
Japan Patent Office, "Decision of Rejection," Japanese Application No. 2024-034923, Dec. 5, 2025.
Korean Intellectual Property Office, "Notice of Final Rejection," Korean Patent Application No. 10-2024-7004222, Nov. 27, 2025.

* cited by examiner

LIGHT THERAPY APPARATUSES

CROSS-REFERENCE TO RELATED APPLICATIONS

This application is a continuation of international patent application no. PCT/US2012/068045, filed pursuant to the Patent Cooperation Treaty on Dec. 5, 2012 and titled "APPARATUSES FOR TREATING AND/OR DIAGNOSING MOTOR-RELATED NEUROLOGICAL CONDITIONS" ("the '045 PCT Application"), which is a continuation-in-part of international patent application no. PCT/US2012/040284, filed pursuant to the Patent Cooperation Treaty on May 31, 2012, and titled "LIGHT-EMITTING APPARATUSES FOR TREATING AND/OR DIAGNOSING MOTOR-RELATED NEUROLOGICAL CONDITIONS" ("the '284 PCT Application"). This application is also a continuation-in-part of the '284 PCT Application, which claims priority to U.S. Provisional Patent Application No. 61/491,864, filed on May 31, 2011, and titled "LIGHT-EMITTING APPARATUSES FOR TREATING AND/OR DIAGNOSING MOTOR-RELATED NEUROLOGICAL CONDITIONS" ("the '864 Provisional Application"). The entire disclosure of each of the '045 PCT Application, the '284 PCT Application and the '864 Provisional Application is, by this reference, incorporated herein.

TECHNICAL FIELD

This disclosure relates generally to apparatuses that expose a subject to wavelengths of light tailored to diagnose one or more motor-related neurological conditions and/or have a therapeutic effect on motor-related neurological conditions. Such a light exposure apparatus may be configured to tailor light that is perceived by the eyes of a subject.

SUMMARY

A light therapy apparatus of the present invention employs a light source. In some embodiments, the light therapy apparatus includes a light-emission apparatus, including the light source, electrical components for operating the light source, and a housing for carrying the light source and the electrical components. In addition, a light-emission apparatus may include controls, which cooperate with one or more of the electrical components to enable a user to control operation of the light source. The controls may provide a user with basic control over the light source; i.e., the ability to turn the light source on and off. In addition, the controls may provide a user with the ability to perform more complex functions including, but not limited to, one or more of: the ability to adjust the intensity of light emitted by the light source; the ability to adjust the color(s) of light emitted by the light source, including ability to tailor the spectrum (or spectra) of light emitted by the light source; and the ability to control a duration of time the light source operates.

In some embodiments, the controls of a light-emission apparatus may comprise one or more processing elements, such as pre-programmed microcontrollers, one or more microprocessors, or the like. The processing element of a light-emission apparatus communicates with the electronics of the light-emission apparatus and, indirectly, with the light source. Accordingly, the processing element may control operation of the light source. In embodiments where the controls of a light-emission apparatus of the present invention include a processing element, the light-emission apparatus may also include associated input elements and output elements and, in some embodiments, communication elements.

In other embodiments, a light therapy apparatus of this disclosure includes one or more filters for limiting one or more wavelengths of light, including visible light, to which a subject is exposed. A filter may be configured for use in conjunction with a light source (e.g., a light emission apparatus, a standard light source, etc.) and, in some embodiments, it may be configured to be coupled or otherwise assembled with the light source. Alternatively, a filter may be configured for use at a location remote from the light source, while still controlling the amounts of light of various wavelengths to which a subject may be exposed.

In one aspect, the present invention includes light therapy apparatuses that are configured to emit light tailored to address motor-related neurological conditions. In various embodiments, such a light therapy apparatus may cause a subject to be exposed to visible light having at least one intensity peak at a wavelength that will treat a motor-related neurological condition, treat a symptom of a motor-related neurological condition, facilitate the repair of retinal cells that may contribute to the motor-related neurological condition or facilitate the repair of neurons that may be responsible for the motor-related neurological condition. That at least one intensity peak may comprise an above ambient or an above average ambient amount of light of its corresponding wavelengths. The visible light that is emitted or to which a subject is exposed may lack above ambient or above average ambient amounts of light (i.e., it may include ambient, average ambient, below ambient or below average ambient amounts of light) that do not treat a motor-related neurological condition, treat a symptom of a motor-related neurological condition, facilitate the repair of retinal cells that may contribute to the motor-related neurological condition or facilitate the repair of neurons that may be responsible for the motor-related neurological condition. Optionally, the visible light that is emitted or to which a subject is exposed may lack above ambient or above average ambient amounts of light (i.e., it may include ambient, average ambient, below ambient or below average ambient amounts of light) that inhibit or regulate the production of neurochemicals, such as monoamines or amines, or eliciting neuroendocrine response.

Examples of wavelengths that treat motor-related neurological conditions or their symptoms include, but are not necessarily limited to, blue-green wavelengths of light and green wavelengths of light, which are also respectively referred to herein as "blue-green light" and "green light" for the sake of simplicity. Without limiting the scope of the present invention, "green light" refers to narrow bandwidths of light (i.e., light of a single wavelength of visible green light or a narrow range of wavelengths of visible green light), as well as to more broad spectrum light (e.g., white light, other polychromatic (i.e., multi-colored) blends of light, etc.) with intensity peaks at one or more wavelengths of green light. "Blue-green light" also includes narrow bandwidths of light and polychromatic light with intensity peaks at one or more wavelengths of blue-green light. A more specific example of light that will treat motor-related neurological conditions or their symptoms includes light that includes above-ambient amounts of wavelengths of 490 nm to 570 nm or of 520 nm to 570 nm. The majority of light (i.e., number of photons, irradiance, etc.) may include one or more wavelengths within either of these ranges; i.e., the light may be enhanced with one or more of these wavelengths.

The light may also lack ambient or above-ambient amounts of other wavelengths of visible light.

Wavelengths of deep red light and near infrared light (e.g., above 650 nm to 900 nm, etc.) may stimulate mitochondrial repair and, thus, repair of the cells, including retinal cells and/or neurons, of which the mitochondria are a part. By using light to stimulate the repair of retinal cells of the eye and/or neurons of the substantia nigra, light may also address the cause of many motor-related neurological conditions.

A light-emission apparatus may be configured to emit visible light (e.g., blue-green and/or green light, deep red light and/or near infrared radiation, etc.) at levels (e.g., intensities, photon densities, irradiances, etc.) that treat one or more motor-related neurological conditions or their symptoms. In various embodiments, one or more therapeutic wavelengths of light may be administered at levels that exceed the corresponding levels of such wavelengths in standard indoor ambient lighting, which levels are referred to herein as "ambient levels." In some embodiments, one or more therapeutic wavelengths of light may be administered at levels that exceed the average levels of these wavelengths of light in standard indoor lighting. These average levels are referred to herein as "average ambient levels."

A light-emission apparatus that is configured to provide therapy for one or more motor-related neurological conditions may be configured to emit insufficient intensities of one or more wavelengths of light that counteract (e.g., enhance, exacerbate, etc.) the symptoms of one or more motor-related neurological conditions. Symptom-exacerbating wavelengths include visible red wavelengths, and could also be considered to include one or more of visible orange and amber wavelengths of light. In some embodiments, such a light-emission apparatus may emit therapeutic light while emitting insufficient intensities of symptom-exacerbating wavelengths of light. In other embodiments, such a light-emission apparatus may emit therapeutic light without emitting or without substantially emitting one or more symptom-exacerbating wavelengths of light. In some embodiments, insufficient intensities may be below ambient or ambient intensities of symptom-exacerbating wavelengths of light. In other embodiments, even above-ambient intensities of symptom-exacerbating wavelengths of light may be insufficient to exacerbate symptoms of a motor-related neurological condition. This may be the case where the symptom-exacerbating wavelengths of light make up only a small portion (e.g., one third of the total intensity or less, etc.) of the total light emitted by the light-emission apparatus or the light to which a subject is exposed.

In some embodiments where a light-emission apparatus is configured to emit above-ambient levels of one or more therapeutic wavelengths of light, the light-emission apparatus may emit ambient amounts of light, below-ambient amounts of light or substantially no light outside of a range of therapeutic wavelengths. In some embodiments, the light source may be configured to emit ambient or below-ambient levels of one or more symptom-exacerbating wavelengths of light. In other embodiments, a light-emission apparatus may emit above-ambient levels of one or more wavelengths of therapeutic light while emitting substantially no light of at least one symptom-enhancing wavelength or no light of at least one symptom-enhancing wavelength of light. Thus, the light source may be configured to emit light consisting essentially of, or even consist of, one or more wavelengths of light that address at least one motor-related neurological condition and light that does not enhance or exacerbate symptoms of the at least one motor-related neurological condition.

In another aspect, a light-emission apparatus of the present invention may be configured to facilitate the early diagnosis of a motor-related neurological condition. Various embodiments of such an apparatus may emit above-ambient levels or intensities of amber, orange and/or red light, or levels or intensities of these wavelengths that are sufficient to exacerbate a symptom of a motor-related neurological condition. In some embodiments, above-ambient intensities of one or more symptom-exacerbating wavelengths of light may be administered to a subject who exhibits some symptoms (including early symptoms) that might be indicative of a motor-related neurological condition, but that do not provide a sure diagnosis of the motor-related neurological condition. In other embodiments, sufficient intensities for exacerbating symptoms of a motor-related neurological condition may be below ambient or ambient intensities of symptom-exacerbating wavelengths of light, such as when symptom-exacerbating wavelengths of light make up a sufficient amount of (e.g., one third or more, a majority of, etc.) the total light emitted by the light-emission apparatus or the light to which a subject is exposed. When administered to such a subject, the sufficient intensity(ies) of one or more wavelengths of symptom-exacerbating light may make the subject's symptoms more pronounced, or may cause the subject to temporarily exhibit previously unexhibited symptoms, which may enable an earlier diagnosis of the motor-related neurological condition. When sufficient intensities of one or more symptom-exacerbating wavelengths of light are administered to a subject who is predisposed to one or more motor-related neurological conditions, the subject may exhibit symptoms of the at least one motor-related neurological condition, which may enable the diagnosis of a motor-related neurological condition in an otherwise symptom-free subject.

In embodiments where a light-emitting apparatus is configured for diagnostic purposes; for example, to emit one or more wavelengths that cause a subject to exhibit symptoms of at least one motor-related neurological condition if the subject is predisposed to or believed to suffer from the at least one motor-related neurological condition, a light source of the diagnostic apparatus may be configured to emit light consisting essentially of, or even consisting of, one or more symptom-enhancing wavelengths of light, along with wavelengths of light that do not counteract the symptom-enhancing wavelengths. Such a diagnostic apparatus may emit no wavelengths of light that are therapeutic for the at least one motor-related neurological condition, substantially no wavelengths of light that are therapeutic for the at least one motor-related neurological condition, or even below-ambient amounts of any wavelength of light that is therapeutic for the at least one motor-related neurological condition.

Other features and advantages of various aspects of the present invention, as well as other aspects of the present invention, will become apparent to those of ordinary skill in the art through consideration of the ensuing description, the accompanying drawings, and the appended claims.

DETAILED DESCRIPTION

Figures 1, 2A, 2B, 2C, 3:
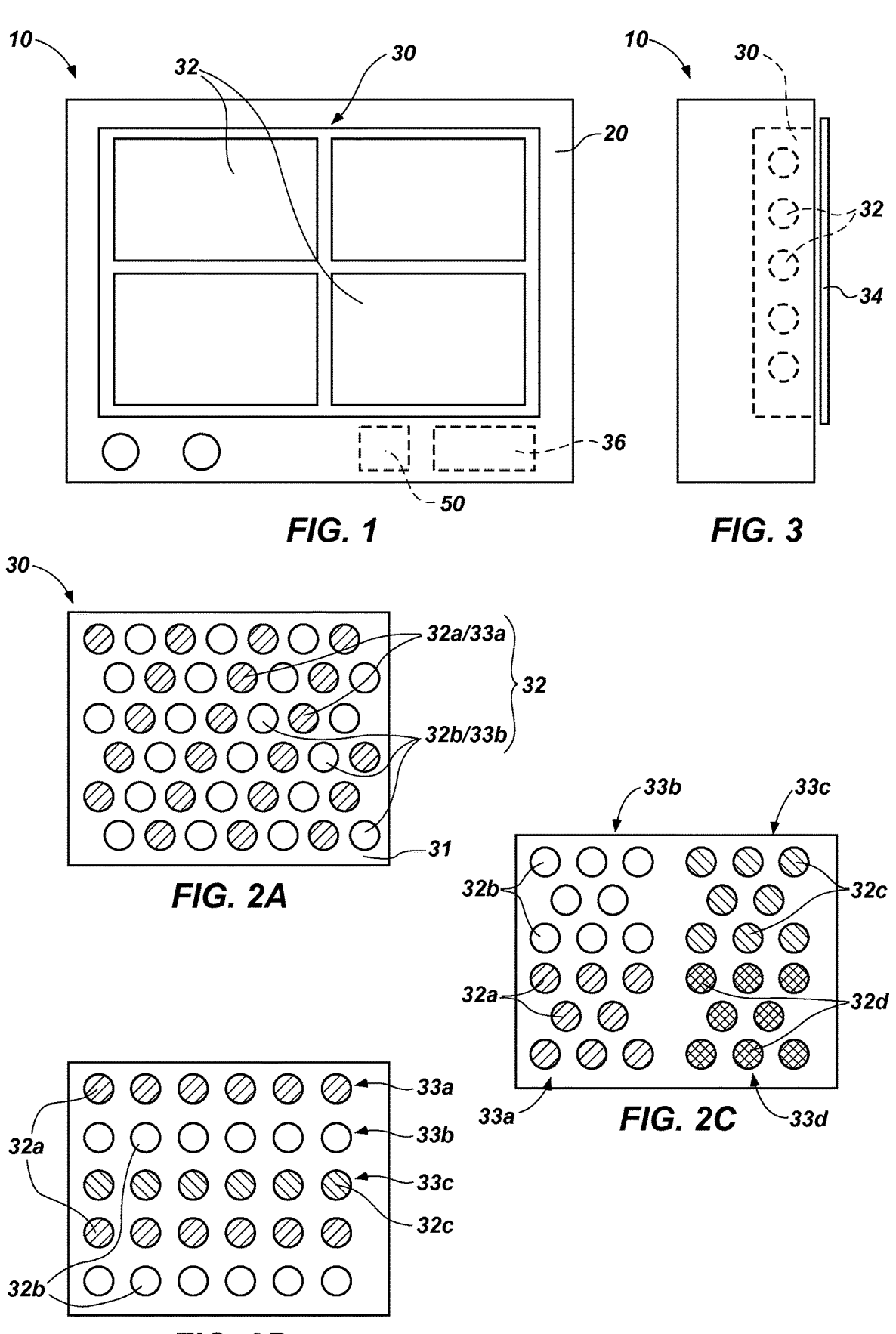
FIG. 1 is a representation of an embodiment of light-emission apparatus according to the present invention, in which the light-emission apparatus is configured to deliver light of at least one wavelength that provides a therapeutic effect for subjects that suffer from at least one motor-related neurological condition.
FIGS. 2A through 2C illustrate lights sources with different arrangements of light emission elements of different colors or bandwidths.
FIG. 3 depicts an embodiment of light-emission apparatus that includes a light source that emits polychromatic light.

FIG. 1 provides a schematic representation of a light-emission apparatus 10 that incorporates teachings of the present invention. In general terms, a light-emission apparatus 10 of the present invention includes a light source 30 and one or more controls associated with the light source 30. The light source 30 may include one or more light emission elements 32, each which may comprise any suitable type of light emitting device known in the art (e.g., a light emitting diode (LED), a fluorescent lamp, a cold cathode fluorescent lamp (CCFL), etc.). Collectively, the light emission elements 32 of the light source 30 may be configured to emit light of one or more desired wavelengths, each at an above-ambient intensity or photon density.

The light source 30 of the light-emission apparatus 10 is, in various embodiments, configured to emit above-ambient levels, or intensities, photon densities or irradiances, of one or more wavelengths of light that are tailored to address one or more motor-related neurological conditions. In some embodiments, the light emitted by the light source 30 may be tailored to address one or more primary symptoms of a motor-related neurological condition. The light emitted by the light source 30 may also be tailored to address one or more secondary symptoms of the motor-related neurological condition (e.g., anxiety, depression, insomnia, hypersomnia, etc.). Additionally, the light emitted by the light source 30 may be tailored to exclude, or at least include insufficient levels or intensities, of wavelengths of light that may exacerbate one or more primary or secondary symptoms of the motor-related neurological condition. In some embodiments, insufficient levels or intensities may be below ambient or ambient levels or intensities of symptom-exacerbating wavelengths of light. In other embodiments, even above-ambient levels or intensities of symptom-exacerbating wavelengths of light may be insufficient to exacerbate symptoms of a motor-related neurological condition, for example, when the symptom-exacerbating wavelengths of light make up only a small portion (e.g., one third of the total intensity or less, etc.) of the total light emitted by the light-emission apparatus or the light to which a subject is exposed.

By way of reference, levels of various wavelengths of light are considered, for purposes of this disclosure, to be "above-ambient" when they exceed the same levels of the same wavelengths of light present in standard indoor lighting. Conversely, for purposes of this disclosure, levels of various wavelengths of light are considered to be "below-ambient" when they are less than the same levels of the same wavelengths of light present in standard indoor lighting. Standard indoor lighting is generally so-called "white light," which is more accurately referred to as "polychromatic light," having an intensity of 50 lux to 500 lux. The term "ambient," when used in the context of levels of one or more wavelengths of light, may refer to the levels of various wavelengths of light present in a particular type of poly-chromatic light at one ambient intensity (e.g., 50 lux, 500 lux, and intensity between 50 lux and 500 lux, etc.), the average levels of various wavelengths of light present in one or more types of polychromatic light at two or more ambient intensities, or the upper and lower levels of one or more wavelengths of light at the upper and lower ends of a range of ambient intensities of polychromatic light from one or more sources.

At about 50 lux, standard indoor lighting (incandescent and/or fluorescent) has a collective photon density of $3.70\times10^{13}$ photons/$cm^2$/s and a collective irradiance of 13.2 $\mu W/cm^2$ (or $1.32\times10^{-5}$ $W/cm^2$). The blue-to-green (e.g., 460 nm to 570 nm, etc.) portion of the spectrum of about 50 lux standard indoor lighting has a photon density of $1.35\times10^{13}$ photons/$cm^2$/s and an irradiance of 5.1 $\mu W/cm^2$. These values, as well as the photon density and irradiance of narrower wavelength ranges in the blue-to-green in standard indoor lighting having an intensity of about 50 lux, are included in the following table:

TABLE 1

| Standard Indoor Light at About 50 lux | | | |
|---|---|---|---|
| Color/Wavelength Range | Photon Density (photons/$cm^2$/second) | Irradiance ($\mu$Watts/$cm^2$) | Lux |
| Polychromatic (white) | $3.70 \times 10^{13}$ | 13.2 | 47 |
| Blue (460 nm to 500 nm) | $3.31 \times 10^{12}$ | 1.4 | 2 |
| Green (500 nm to 570 nm) | $1.03 \times 10^{13}$ | 3.8 | 22 |
| Blue-to-Green (460 nm to 570 nm) | $1.35 \times 10^{13}$ | 5.1 | 23 |
| 490 nm to 565 nm | $1.02 \times 10^{13}$ | 3.8 | 20 |
| 520 nm to 565 nm | $7.25 \times 10^{12}$ | 2.6 | 17 |
| 525 nm to 555 nm | $4.81 \times 10^{12}$ | 1.8 | 11 |
| 520 nm to 539 nm | $2.68 \times 10^{12}$ | 1.0 | 6 |

The amber-to-red (e.g., above 570 nm to 640 nm, etc.) portion of the spectrum of about 50 lux standard indoor lighting has an intensity of about 24 lux, a photon density of $2.04\times10^{13}$ photons/$cm^2$/s and an irradiance of 6.7 $\mu W/cm^2$. The irradiance of amber-to-red light in standard indoor lighting at about 50 lux exceeds the irradiance of the blue-to-green "effective" spectrum of standard indoor lighting at about 50 lux.

At about 500 lux, the collective photon density of standard indoor lighting is $3.69\times10^{14}$ photons/$cm^2$/s and the collective irradiance of standard indoor lighting is 133.5 $\mu W/cm^2$. At about 500 lux, the blue-to-green portion of the standard indoor lighting spectrum has a photon density of $1.53\times10^{14}$ photons/$cm^2$/s and an irradiance of 58.4 $\mu W/cm^2$. These values, as well as the photon density and irradiance of narrower wavelength ranges in the blue-to-green in standard indoor lighting having an intensity of about 500 lux, are included in the following table:

TABLE 2

| Standard Indoor Light at About 500 lux | | | |
|---|---|---|---|
| Color/Wavelength Range | Photon Density (photons/$cm^2$/second) | Irradiance ($\mu$Watts/$cm^2$) | Lux |
| Polychromatic (white) | $3.69 \times 10^{14}$ | 133.5 | 479 |
| Blue (460 nm to 500 nm) | $4.09 \times 10^{13}$ | 16.9 | 18 |
| Green (500 nm to 570 nm) | $1.14 \times 10^{14}$ | 42.0 | 238 |
| Blue-to-Green (460 nm to 570 nm) | $1.53 \times 10^{14}$ | 58.4 | 256 |
| 490 nm to 565 nm | $1.15 \times 10^{14}$ | 42.9 | 223 |

TABLE 2-continued

| Standard Indoor Light at About 500 lux | | | |
|---|---|---|---|
| Color/Wavelength Range | Photon Density (photons/cm²/second) | Irradiance (μWatts/cm²) | Lux |
| 520 nm to 565 nm | $7.79 \times 10^{13}$ | 28.5 | 181 |
| 525 nm to 555 nm | $5.14 \times 10^{13}$ | 18.9 | 121 |
| 520 nm to 539 nm | $3.03 \times 10^{13}$ | 11.4 | 66 |

The amber-to-red portion of the spectrum of about 500 lux standard indoor lighting has an intensity of about 225 lux, a photon density of $1.85 \times 10^{14}$ photons/cm²/s and an irradiance of 60.4 μW/cm². The irradiance of amber-to-red light in standard indoor lighting at about 500 lux exceeds the irradiance of the blue-to-green "effective" spectrum of standard indoor lighting at about 500 lux.

Based on the foregoing, when "ambient" includes an average of the level of one or more bandwidths of light in polychromatic light of about 50 lux and the level of the same bandwidth(s) of light in polychromatic light of about 500 lux, the ambient levels of the bandwidths set forth in TABLES 1 and 2 may include the ambient values for standard indoor lighting identified in TABLE 3.

TABLE 3

| Average Ambient Levels of Standard Indoor Light | | | |
|---|---|---|---|
| Color/Wavelength Range | Photon Density (photons/cm²/second) | Irradiance (μWatts/cm²) | Lux |
| Polychromatic (white) | $2.03 \times 10^{14}$ | 73.4 | 263 |
| Blue (460 nm to 500 nm) | $2.21 \times 10^{13}$ | 9.1 | 10 |
| Green (500 nm to 570 nm) | $6.19 \times 10^{13}$ | 22.9 | 130 |
| Blue-to-Green (460 nm to 570 nm) | $8.35 \times 10^{13}$ | 31.8 | 140 |
| 490 nm to 565 nm | $6.24 \times 10^{13}$ | 23.4 | 122 |
| 520 nm to 565 nm | $4.26 \times 10^{13}$ | 15.6 | 99 |
| 525 nm to 555 nm | $2.81 \times 10^{13}$ | 10.3 | 66 |
| 520 nm to 539 nm | $1.65 \times 10^{13}$ | 6.2 | 36 |

The amber-to-red portion of the spectrum of ambient standard indoor lighting has an intensity of about 125 lux, a photon density of $1.03 \times 10^{14}$ photons/cm²/s and an irradiance of 33.6 μW/cm². The irradiance of amber-to-red light in standard indoor lighting of average intensity exceeds the irradiance of the blue-to-green "effective" spectrum of standard indoor lighting at average intensity.

As an alternative to defining "ambient" in terms of an average, "ambient" light may include polychromatic light within a range of intensities, photon densities and/or irradiances, or energies, along with the levels of light within various bandwidths of polychromatic light within such a range. Levels of various wavelengths of light may be considered to be "above-ambient" when they exceed the same levels of the same wavelengths of light in an ambient range. Conversely, levels of various wavelengths of light may be considered to be "below-ambient" when they are less than the same levels of the same wavelengths of light present in the ambient range. For purposes of this disclosure, the low end of "ambient" levels may comprise the levels of each wavelength range present in about 50 lux polychromatic light, while the high end of "ambient" levels comprises the levels of various wavelength ranges present in about 500 lux polychromatic light. With this definition of ambient, below-ambient levels would include below-about 50 lux levels, while above-ambient levels would include above-about 500 lux levels.

As a point of reference, incandescent indoor lighting, which has a collective ambient intensity of about 50 lux to about 500 lux, is composed primarily of amber and red wavelengths of light, with some green light. Green light makes up only a small portion of the spectrum output by incandescent indoor lighting. Thus, the intensity of the green wavelengths present in incandescent indoor lighting is significantly less than 200 lux. Fluorescent indoor lighting has the signature of mercury, with three intensity peaks: a first peak in the indigo-deep blue range (435 nm-436 nm); a second peak in the green-yellow range (540 nm-560 nm); and a third peak at the red wavelength from 580 nm to 640 nm. As with incandescent indoor lighting, the intensity of fluorescent indoor lighting is only about 50 lux to about 500 lux. The deep blue and green-yellow peaks of such light are, of course, less intense than the collective intensity of light output by fluorescent indoor lighting.

As an option to characterizing light in terms of its level or intensity relative to ambient levels, the light that is administered to a subject in connection with the diagnosis or treatment of a motor-related neurological condition (or for any other purpose) may characterized in terms of the relative proportions or ratios of certain wavelengths, bandwidths and/or intensity peaks. Without limitation, when the light emitted by a light source has a particular effect, the intensity or irradiance of the wavelength(s) of light responsible for that effect a light source may make up a certain proportion or ratio of the overall light emitted by that light source (e.g., more than a third, more than half, more than two-thirds, 95% or more, etc.). The following table compares the ratios of red to non-red visible light of five (5) available light sources (the BRITE LITE 6, the LITEBOOK ELITE, the CRI LITE, the BRITE LITE 3 and the NORTHSTART) to two light sources that have been configured to incorporate teachings of this disclosure (the SPECTRAMAX).

TABLE 4

| Light Source | Total Visible Irradiance μW/cm3 380 nm to 780 nm | Yellow/ Green μW/cm3 520 nm to 570 nm | Red μW/cm3 579 nm to 649 nm | Ratio of Red to Non-Red Visible Light Ratio of 571 nm to 649 nm to 380 nm to 780 nm excluding 571 nm to 649 nm | Ratio of Red to Yellow/Green Ratio of 571 nm to 649 nm to 520 nm to 570 nm |
|---|---|---|---|---|---|
| Brite Lite 6 | 584 | 154 | 149 | 34.3% | 97% |
| LiteBook Elite | 530 | 131 | 198 | 59.6% | 151% |
| CRI Lite | 1322 | 359 | 414 | 45.6% | 115% |
| Brite Lite 3 | 1749 | 484 | 760 | 76.8% | 157% |
| NorthStar | 1828 | 528 | 541 | 42.0% | 102% |
| SpectraMax | 643 | 169 | 67 | 11.6% | 40% |
| SpectraMax | 270 | 71 | 67 | 33.0% | 94% |

The data from TABLE 4 indicate that of all the visible total intensity of light emitted by the first SPECTRAMAX sample, which provides a therapeutic effect for motor-related neurological conditions, the amount of red light emitted is only 11.6% of the amount of all other wavelengths of visible light emitted, and the level of red light emitted is only 40% of the level of blue-green light emitted. The second SPECTRAMAX also provides effective therapy for motor-related neurological conditions, and emits 33% as much red light as all other wavelengths of visible light, and 94% as much red light as blue-green light. When the amount of red light emitted by a light source is at most 33% of the amount of all other wavelengths of visible light emitted by that light source and/or the amount of red light emitted by the light source is at most 95% of the blue-green light emitted by that light source, that light source may be useful for treating a motor-related neurological condition.

When administered to the eyes of a subject (i.e., ocularly) in above-ambient levels, light within the range of blue wavelengths (e.g., minimum wavelength of 460 nm, etc.) to blue-green wavelengths (e.g., minimum wavelength of 490 nm, etc.) to green wavelengths (e.g., maximum wavelength of 570 nm, etc.) has a positive, or beneficial, effect on motor-related neurological conditions and their symptoms, including both primary and secondary symptoms. See, e.g., International patent application no. PCT/IB2012/002553, titled "METHODS FOR PREVENTING AND TREATING MOTOR-RELATED NEUROLOGICAL CONDITIONS," filed on Dec. 3, 2012 (the "'553 PCT Application"), the entire disclosure of which is, by this reference, hereby incorporated herein. It is believed that the administration of light including above-ambient intensity peaks centered at any location within the blue-green to green range of wavelengths will benefit subjects who suffer from motor-related neurological conditions.

The ocular administration of above-ambient levels of any of these wavelengths of light may stimulate a dopaminergic response in the body of a subject, which may in some instances vary levels or activity of one or more monoamines (e.g., melatonin, serotonin, dopamine, derivatives and/or analogs of the foregoing, etc.), restore a balance of chemicals in the brain of a subject (e.g., moderate (e.g., decrease, etc.) melatonin production by the subject, moderate (e.g., increase, etc.) dopamine and/or serotonin production by the subject, etc.), with the degree of restoration and/or moderation being a function of the wavelength(s) and/or the level(s) of light administered to the subject. Light therapy with an apparatus that incorporates teachings of the present invention stimulate a dopaminergic response, which can restore or provide balance to levels of one or more monoamines (e.g., melatonin, serotonin dopamine, etc.) in a subject's brain. For the sake of simplicity, the terms "melatonin," "serotonin" and "dopamine," as used herein, respectively include melatonin and analogs or derivatives of melatonin, serotonin and analogs of serotonin and dopamine and analogs or derivatives of dopamine. Amounts or levels of one or more monoamines within the body of a subject may be adjusted in a manner that addresses a motor-related neurological condition. The adjustment of monoamine levels in the body of a subject includes, but is not necessarily limited to, adjusting or balancing melatonin or serotonin levels at particular times of the day (e.g., late afternoon, early evening, etc.).

Light within the range of amber wavelengths (e.g., wavelengths of more than 570 nm, etc.) to red wavelengths (e.g., maximum wavelength of 650 nm, 750 nm, etc.), when ocularly administered to a subject in sufficient levels, may exacerbate any motor-related neurological conditions from which the subject may suffer, or at least one of the symptoms of any such motor-related neurological condition. See, e.g., the '553 PCT Application. Specifically, exposure to amber, orange and red wavelengths of light may cause a subject who is predisposed to a motor-related neurological condition and/or a subject who suffers from, but has not yet clearly exhibited symptoms of one or more motor-related neurological conditions, to exhibit one or more symptoms of the motor-related neurological condition. Moreover, when the eyes of a subject are exposed to sufficient levels of amber to red wavelengths of light (e.g., light having wavelengths of greater than 570 nm, up to 650 nm; of greater than 570 nm, up to 750 nm; etc.), dopaminergic activity by the subject's body may be temporarily inhibited (e.g., melatonin production by the subject may be enhanced, dopamine production by the subject may be inhibited, etc.). Above-ambient levels or intensities of symptom-exacerbating wavelengths of light may be sufficient to exacerbate symptoms of a motor-related neurological condition. In some embodiments, sufficient levels or intensities may be below ambient or ambient levels or intensities of symptom-exacerbating wavelengths of light, such as when symptom-exacerbating wavelengths of light make up a sufficient amount of (e.g., one third or more, a majority of, etc.) the total light emitted by the light-emission apparatus or the light to which a subject is exposed.

Wavelengths of electromagnetic radiation above 650 nm, including visible light and infrared radiation, may promote or stimulate mitochondrial repair. In the eyes, the promotion or stimulation of mitochondrial repair may facilitate the repair of damaged retinal cells, which damage may be at least partially responsible for motor-related neurological conditions, and, thus, at least partial avoidance and/or reversal of the motor-related neurological condition. In the substantia nigra, the promotion or stimulation of mitochondrial repair may facilitate repair of damaged neurons responsible for a motor-related neurological condition and, thus, at least partial reversal of the motor-related neurological condition.

As indicated previously herein, the light source 30 of a light-emission apparatus 10 may be configured to emit light of one or more predetermined, and relatively narrow bandwidths, or wavelength ranges. The light source 30 may be configured to address a motor-related neurological condition, or at least one or more primary and/or secondary symptoms of such a condition. The light source 30 may be configured to emit light that causes a subject to elicit a neurological or neuroendocrine response. The light emitted by the light source 30 may have a therapeutic effect on one or more motor-related neurological conditions or their symptoms. A light-emission apparatus 10 of the present invention may be configured to stimulate a dopaminergic response, which may moderate levels of one or more monoamines in the body of a subject (e.g., by affecting the production of melatonin, serotonin and/or dopamine by the subject, etc.). A decrease in certain monoamine levels may result from stimulation of the subject's body to decrease production of those monoamines or in any other manner. Likewise, an increase in other monoamine levels may result from stimulation of the subject's body to increase production of those monoamines. For example, certain wavelengths of light may stimulate dopamine, serotonin, etc., while suppressing or decreasing the production of melatonin. Thus, in some embodiments, the light source 30 of a light-emission apparatus 10 may be configured to emit light that provides a desired change in the subject's monoamine levels.

In some embodiments, the light source 30 may be configured to emit, at an above-ambient level, light that addresses the motor-related neurological condition or any of its symptoms in a positive manner (e.g., at least one bandwidth of light with at least one intensity peak centered in the range of 460 nm to 570 nm, inclusive; in the range of 490 nm to 570 nm, inclusive; in the range of 520 nm to 570 nm, inclusive; etc). The desired therapeutic effect may be achieved by ocularly exposing a subject to an above-ambient level of at least one bandwidth of light with the at least one intensity peak centered in the range of blue to green light (e.g., 460 nm to 570 nm, inclusive), blue-green to green light (e.g., 490 nm to 570 nm, inclusive) or green light (e.g., 520 nm to 570 nm, inclusive). The at least one intensity peak may comprise the most intense peak of visible light to which a subject is exposed. As another option, the majority of light to which the subject is exposed may be within one or more of the blue to green, blue-green to green or green light ranges and, thus, may be said to be "enhanced" with one or more of these colors of visible light. As a non-limiting example, the light therapy apparatus may be configured to expose a subject to light tailored to stimulate a dopaminergic response, which may cause changes in the levels of, or balance the ratio of, one or more monoamines (e.g., a decrease in the level of melatonin, an increase in the level of dopamine and/or serotonin, etc.) in the subject's body.

Such an embodiment of light source 30 may also be configured to emit ambient levels of light, below-ambient levels of light or substantially no light outside of the therapeutic range. In a more specific embodiment, the light source 30 may be configured to emit ambient or below-ambient levels of light that may exacerbate the motor-related neurological condition, or one or more of its symptoms. As an even more specific example, the light source 30 may be configured to emit ambient or below-ambient levels of light that may inhibit dopaminergic activity by the body of a subject. Even more specifically, the light source 30 may be configured of emit ambient or below-ambient levels of light that may increase melatonin levels or decrease dopamine or serotonin levels within the body of a subject. Above-ambient dosages of bandwidths of light with intensity peaks centered at more than 570 nm to 650 nm, at more than 570 nm to 750 nm, etc., are known to exacerbate motor-related neurological conditions or their symptoms and to inhibit dopaminergic activity, and are believed to increase melatonin levels and decrease dopamine and serotonin levels.

In another aspect, a light-emission apparatus 10 may include a light source 30 configured to exacerbate one or more motor-related neurological conditions or their symptoms experienced by a subject. Without limitation, the light source 30 may be configured to temporarily inhibit a dopaminergic response by a subject (e.g., increase melatonergic activity within the body of a subject, decrease levels of dopamine within the body of the subject, decrease dopaminergic activity, etc.). One or more motor-related neurological conditions may be exacerbated by ocularly exposing the subject to at least one bandwidth of light with a peak centered in the range of more than 570 nm to 750 nm, inclusive. This effect may also be achieved with ambient or below-ambient levels of light with at least one bandwidth of light peaking in the range of 570 nm to 750 nm, when that light is isolated from or produces a higher ratio of light than the range of 460-570 nm. In some embodiments, such a light source 30 may be configured not to emit above-ambient levels of light that may be therapeutic for any of the motor-related neurological conditions or their symptoms. In other embodiments, such a light source 30 may be configured to emit light where the ratio of 570-750 nm light is greater than the ratio of 460-570 nm light. Any of these concepts may be useful for stimulating melatonin production by the subject and, thus, increasing melatonergic response in the subject's body.

In yet another example, a light source 30 may be configured to moderate the level of one or more monoamines within the body of a subject by selectively exposing the subject to light that may increase levels of one or more monoamines (while possibly decreasing levels of one or more other monoamines in the subject's body) within the subject's body or to light that may decrease levels of one or more monoamines within the subject's body (while possibly increasing or balancing levels of one or more other monoamines in the subject's body).

A light-emission apparatus 10 may include a light source 30 that enables the early detection of one or more motor-related neurological conditions. As noted above, ocular exposure of a subject to amber to red wavelengths of light (e.g., more than 570 nm to 650 nm, more than 570 nm to 750 nm etc.) may cause a subject who is predisposed to a motor-related neurological condition or who suffers from, but does not yet clearly exhibit symptoms of, a motor-related neurological condition to exhibit symptoms of that condition. By emitting above-ambient levels of such light, a light source 30 may cause one or more symptoms of a motor-related neurological condition in such a subject to emerge. Thus, a light-emission apparatus 10 of the present invention may include a light source 30 that may enable early diagnosis of a motor-related neurological condition to which a subject is predisposed or a motor-related neurological condition from which the subject already suffers without otherwise exhibiting clear symptoms.

The light source 30 of a light-emission apparatus 10 that incorporates teachings of the present invention may be configured to emit one or more wavelengths of light that may stimulate mitochondrial repair. By stimulating retinal repair, it is currently believed that the wavelength or wavelengths of light emitted by a light-emission apparatus 10 of the present invention may repair damaged retinal cells and/or damaged neurons. It is currently believed that repairing damaged retinal cells may at least partially prevent and/or reverse motor-related neurological conditions. It is also currently believed that repairing damaged neurons, such as the neurons of the substantia nigra, may at least partially reverse motor-related neurological conditions. In some embodiments, such a light source 30 may be configured to emit light having wavelengths of more than 650 nm, which may include deep red (visible) light and some infrared radiation (e.g., wavelengths of infrared radiation of about 1,400 nm or less, of about 900 nm or less, etc.).

A light-emission apparatus 10 of the present invention may include a light source 30 that only emits light that will provide a single result (e.g., one of the foregoing functions, etc.). Alternatively, the light source 30 may be configured with selectivity that enables a user to choose a desired function from a plurality of functions (e.g., any combination of the functions described above, etc.).

In embodiments where the light-emission apparatus 10 is configured to provide a single result, the light source 30 may be configured to emit sufficient levels of one or more wavelengths of light that may achieve the desired result. These wavelengths of light are referred to herein as "desirable wavelengths." In addition, the light source 30 may be configured not to emit above-ambient levels of any wavelengths of light that may counteract the desired result (i.e., the light source 30 may emit ambient levels of such wavelengths or below-ambient levels of such wavelengths), which wavelengths of light are referred to herein as "undesirable wavelengths." In some embodiments, the only wavelengths of light that may be emitted by the light source 30 at above-ambient levels are desirable wavelengths. In other embodiments, the light source 30 may be configured to only emit desirable wavelengths of light.

The light emission characteristics of the light source 30 may be defined by the light emission element(s) 32 of the light source 30. A variety of embodiments of light emission elements 32 that emit one or more relatively narrow bandwidths of light may be used in the light source 30 of a light-emission apparatus that incorporates teachings of the present invention. Without limiting the scope of the present invention, the light emission elements 32 may comprise light emitting diodes (LEDs). LEDs may be configured to emit predefined narrow bandwidths of light, including a variety of desirable wavelengths. LEDs may also be configured to not emit undesirable wavelengths of light, to emit undesirable wavelengths of light at below-ambient levels, or to emit undesirable wavelengths of light at levels that do not exceed ambient levels of such wavelengths.

Alternatively, the light emission element(s) 32 may emit desirable wavelengths of light along with light of one or more other wavelengths. Such a light emission element 32 is referred to in the art as a "polychromatic light source." The other wavelengths of light emitted by the light emission element(s) 32 may include undesirable wavelengths, or they may consist of innocuous and/or other helpful wavelengths of light. In embodiments where the light emission element(s) 32 generate(s) light of one or more undesirable wavelengths at undesirably high levels (e.g., any emission of such wavelengths, ambient levels of such wavelengths, above-ambient levels of such wavelengths, etc.), the light source 30 may include one or more filters 34 to attenuate the emission of the one or more undesirable wavelengths from the light-emission apparatus 10. As known in the art, filters 34 may be selected on the basis of the wavelengths of light they attenuate.

One or more filters 34 may also be used in conjunction with a light source 30 that generates one or more narrow bandwidths of light.

Some embodiments of light-emission apparatuses 10 that incorporate teachings of the present invention are configured to be used for multiple functions (e.g., any combination of the above-described functions, etc.). The light source 30 of such a light-emission apparatus 10 may be configured to enable a user to select a desired function from a plurality of functions.

As a non-limiting example, a light-emission apparatus 10 may include a light source 30 with two or more sets 33a, 33b, etc., of light emission elements 32, as shown in FIG. 2A. Each set 33a, 33b, etc., may include light emission elements 32a, 32b, etc., that perform a different function from the light emission elements 32a, 32b, etc., (collectively, "light emission elements 32") of every other set 33a, 33b, etc. In the illustrated embodiment, the light emission elements 32 may be organized over an emission surface 31 of the light source 30 in an array, with light emission elements 32a, 32b, etc., from different sets 33a, 33b, etc., respectively, interspersed, or mixed, with one another. Alternatively, as illustrated by FIG. 2B, the light emission elements 32 may be organized in alternating rows or columns, with each row or column consisting of or primarily comprising light emission elements 32a, 32b, etc., of a single type. As another alternative, each different type of light emission elements 32a, 32b, etc., may be grouped together, as depicted by FIG. 2C.

In some embodiments, one set 33a of light emission elements 32a may be configured to address a motor-related neurological condition or one or more symptoms of such a condition. Another set 33b of light emission elements 32b may be configured to facilitate diagnosis of a motor-related neurological condition. Another optional set 33c of light emission elements 32c may be configured to repair cellular damage (e.g., mitochondrial damage, etc.) to retinal cells and/or neurons that may cause the motor-related neurological condition. In a specific embodiment, a light source 30 may be configured to emit sufficient levels of light that will address a motor-related neurological condition (e.g., 490 nm to 570 nm, 520 nm to 570 nm, etc.) and light that will repair cellular damage (e.g. 650 nm or greater, etc.), while emitting insufficient levels of light that will exacerbate a symptom of a motor-related neurological condition (e.g., greater than 570 nm to less than 650 nm, etc.).

As another example, a light-emission apparatus 10 may be configured to moderate levels of one or more monoamines in the body of a subject. Such a light-emission apparatus 10 may include a light source 30 with one set 33a of light emission elements 32a that emit light that may treat a motor-related neurological condition or its symptoms, such as by stimulating a dopaminergic response by a subject's body (e.g., cause a decrease in melatonin levels or melatonergic activity (e.g., by stimulating the body of a subject to suppress or delay the production of melatonin and/or increase serotonin production, etc.); cause an increase in dopamine levels (e.g., by stimulating the subject's body to increase dopamine production, etc.); etc.) and another set 33b of light emission elements 32b that may exacerbate a motor-related neurological condition or its symptoms (e.g., cause an increase in melatonin levels or melatonergic activity, or diminishing serotonergic activity, etc., (e.g., by stimulating the body of the subject to produce more melatonin and/or reduce serotonin, etc.); cause a decrease in dopamine levels (e.g., by stimulating the body of the subject to cease or slow down dopamine production, etc.); etc.).

The light-emission apparatus 10 may perform different functions at discrete points in time (e.g., diagnose a motor-related neurological condition/address a motor-related neurological condition or its symptoms; elicit a neurological response; elicit a neuroendocrine response; increase or decrease levels of certain neurochemicals, such as monoamines; etc.). Alternatively, at least portions of the performance of two or more functions by the light-emission apparatus 10 may be effected simultaneously (e.g., address a motor-related neurological condition/promote cellular repair; etc.).

The manner in which different functions are to be performed by such a light source 30 may be controlled with a processing element 36, such as a microcontroller, of a type known in the art. The processing element 36 of the light source 30 may be pre-programmed to perform a set of defined functions. In some embodiments, parameters of the defined functions (e.g., duration of operation; intensity, photon density and/or irradiance; etc.) may be defined by programming of the processing element 36. In other embodiments, the processing element 36 may be programmed with one or more parameters (e.g., duration of operation; intensity, photon density and/or irradiance; wavelength(s) of light emitted; etc.) that control the manner in which light is emitted by the light source 30 and, thus, the function to be performed by the light-emission apparatus 10. In some embodiments, the processing element 36 and the light source 30 may be configured in a manner that enables a light-emission apparatus 10 of the present invention to emit different spectra based on a number of different factors. As a non-limiting example, the processing element 36 and the light source 30 of a light emission apparatus 10 may be configured to cause the light-emission apparatus 10 to emit different intensities of different wavelengths of light at different times during a day. A specific embodiment of such a light-emission apparatus 10 may be configured to counteract the effects of natural light at different times of the day (e.g., to generate and emit blue-green and/or green light at increasingly greater intensities as the time of day progresses from afternoon to evening; to generate and emit decreasingly lesser intensities of amber, orange and red light as the time of day progresses from afternoon to evening; etc.). As another example, the processing element 36 and the light source 30 of a light-emission apparatus 10 may be configured to cause the light-emission apparatus 10 to emit different spectra based upon the particular symptom(s) experienced by a subject and/or the severity of each symptom.

Turning now to FIG. 3, an embodiment of light-emission apparatus 10 that includes a light source 30 that generates polychromatic light is depicted. In some embodiments, the polychromatic light may comprise so-called "white" light emitted by one or more light emission elements 32. In other embodiments, light of a plurality of different colors simultaneously emitted by a plurality of differently configured light emission elements 32 may blend to provide the polychromatic light. In any event, the polychromatic light emitted by the light source 30 includes various wavelengths and/or bandwidths that will perform a plurality of desired functions.

As those of ordinary skill in the art understand, the specific characteristics of polychromatic light (e.g., the wavelengths of light included in polychromatic light, the wavelengths at which relative intensity peaks of certain colors of light are centered, etc.) depend upon the source(s) (e.g., the light emission elements 32, etc.) of that polychromatic light. These specific characteristics of polychromatic light from various sources may be referred to as the "signature" of the polychromatic light.

The signature of the polychromatic light emitted by the light source 30 of a light-emission apparatus 10 may at least partially define the function or functions that the light-emission apparatus 10 is capable of performing. As an example, a light-emission apparatus 10 that includes a light source 30 that emits polychromatic light with peaks of blue, blue-green and/or green light (i.e., the desirable wavelengths in this example) may be useful for addressing a motor-related neurological condition, for addressing a motor-related neurological condition or its symptoms, or for stimulating a dopaminergic response by the subject, which may cause changes in levels of one or more monoamines within a subject's body. This is particularly true where the magnitude of a peak of one or more desirable wavelengths exceeds the magnitude of a peak of any undesirable wavelength, or color, of light (e.g., amber, orange or red light) that may counteract the effectiveness of the desirable wavelength(s) (e.g., blue, blue-green and/or green light), and especially where the relative magnitudes of the peaks of desirable and undesirable wavelengths enables the polychromatic light to be delivered in such a way that desirable wavelengths of light are provided at above-ambient levels while undesirable wavelengths of light are provided at ambient levels or below-ambient levels. In some embodiments, the light source 30 of a light-emission apparatus 10 of the present invention may be configured to emit unfiltered polychromatic light.

The function or functions that are to be performed by a light source 30 with light emission elements 32 that emit polychromatic light may also be defined by controlling the wavelength(s) and/or bandwidth(s) of light emitted by the light source 30. Thus, the light source 30 of a light-emission apparatus 10 of the present invention may include one or more filters 34 that at least partially block, or attenuate, any wavelength(s) of light that may counteract the desired function(s), while allowing for the transmission of therapeutic levels of certain desirable wavelengths and amounts (e.g., intensities, irradiances, etc.) of light and, thus, the emission of such desirable wavelengths of light from the light source 30. The use of different filters 34 may enable the light-emission apparatus 10 to perform different functions.

With renewed reference to FIG. 1, in addition to a light source 30, a light-emission apparatus 10 of the present invention may include a housing 20. The housing 20 carries the light source 30. In addition, the housing 20 may carry one or more other components of the light-emission apparatus 10, including, but not limited to, controls for operating the light source 30 and a power supply 50. A light-emission apparatus 10 of the present invention may also include any of a variety of other features (e.g., a light transmission lens, features for diffusing the emitted light, features for focusing the emitted light, features for orienting the housing 20, etc.) that may provide it with desired functionality.

The housing 20 of a light-emission apparatus 10 that incorporates teachings of the present invention may have any suitable configuration. In embodiments where the light-emission apparatus 10 is configured to deliver light-emission in controlled conditions (e.g., in a research facility, in a medical clinic, etc.) or is intended for repeated use in substantially the same location, the housing 20 may be relatively large (e.g., so as to accommodate a relatively large light source 30, etc.). Due to its size, such a light-emission apparatus 10 may lack portability. Accordingly, the power supply 50 of such a light-emission apparatus 10 may comprise components that enable the light-emission apparatus 10 to operate under AC power, in a manner known in the art.

In other embodiments, a more portable light-emission apparatus 10 may be desirable. The housing 20 of the light-emission apparatus 10 may be configured to, at least in part, impart the light-emission apparatus 10 with portability and, in some embodiments, enable the light-emission apparatus 10 to perform its desired function(s) as it is held by a user's hand. In various embodiments, such a housing 20 may be readily transportable, occupy minimal space during transportation and/or storage and be configured to enable the light-emission apparatus 10 to be used in a variety of setting or under a variety of circumstances. In addition to including a small housing 20, a portable light-emission apparatus 10 may include a correspondingly small, even lightweight, light source 30. In some embodiments, the power supply 50 of a portable light-emission apparatus 10 may include one or more batteries, further imparting the light-emission apparatus 10 with portability. Portable embodiments of light emission apparatuses 10 of the present invention may be configured to be positioned on a surface (e.g., a tabletop, the subject's lap, etc.), to be worn by the subject receiving light therapy (e.g., head-mountable to direct light to the subject's eyes from above (e.g., like a visor or hat, etc.), from below and/or around the periphery of the subject's eyes (e.g., like glasses, etc.); etc.) or have any other suitable configuration.

In some embodiments, a light-emission apparatus 10 may include a processing element (e.g., a microprocessor, a microcontroller, etc.) and a light source 30.

In use, a light-emission apparatus 10 of the present invention may be configured to direct light toward the eyes of a subject and, thus, to provide ocular light therapy. In some embodiments, the subject's eyes may be closed while ocular light therapy is provided. In other embodiments, a subject may open his or her eyes as ocular light therapy is provided. In further embodiments, desired ocular light therapy may be provided regardless of whether the subject's eyes are open or closed.

Figure 4:
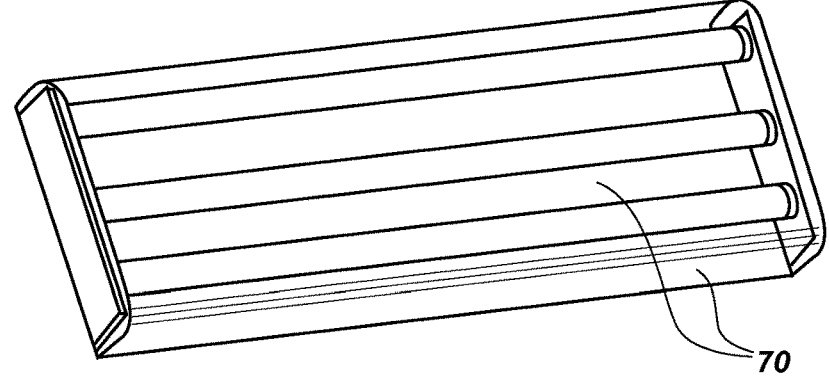
FIGS. 4 through 6 illustrate some embodiments of filters that may be used to control the amounts of light of one or more wavelengths to which a subject is exposed.
Figure 5:
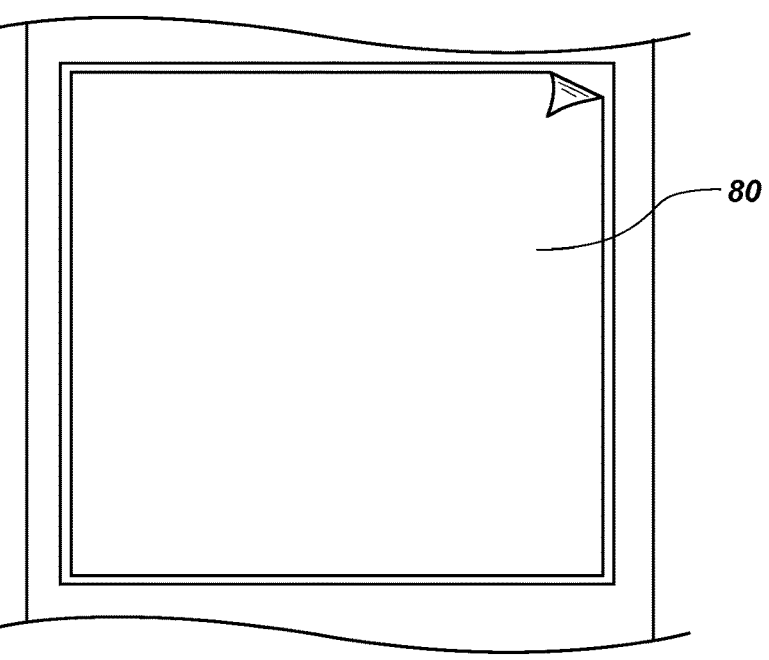
Figure 6:
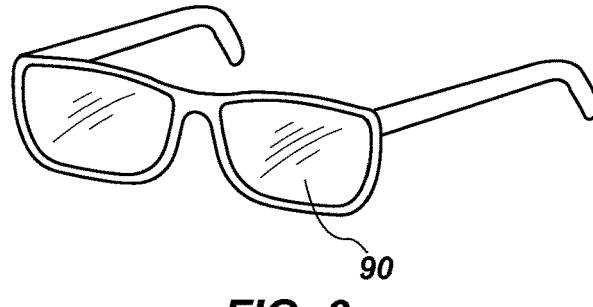

Turning now to FIGS. 4 through 6, various embodiments of light therapy apparatuses that employ filters are illustrated. FIG. 4 illustrates an embodiment of a filter 70 that is configured to be positioned over a standard light source, such as a light bulb 72 for limiting wavelengths of light that are emitted beyond the light source 72. FIG. 5 depicts an embodiment of filter 80 that is configured to be placed over a subject's eyes to limit the wavelengths or amounts of various wavelengths of light (e.g., natural light, artificial light, etc.) to which the subject's eyes are exposed; for example, in the form of a lens or a pair of lenses. FIG. 6 shows an embodiment of filter 90 that comprises window tinting for limiting wavelengths of light (e.g., natural light, artificial light, etc.) to which a subject may be exposed.

Each filter 70, 80, 90 may be configured to tailor exposure of a subject to certain wavelengths of light and/or to certain amounts of certain wavelengths of light. Without limitation, a filter 70, 80, 90 may be tailored to enable the subject to be exposed to one or more therapeutic, diagnostic or restorative wavelengths of light. The filter 70, 80, 90 may be configured in such a way that the subject is exposed to one or more above-ambient amounts of some wavelengths of light and ambient or below-ambient amounts of one or more other wavelengths of light, as disclosed previously herein.

In a more specific embodiment, a filter 70, 80, 90 may be used to reduce the amounts of visible light having wavelengths above 570 nm, or at least in the range of 575 nm to 640 nm, to below-ambient levels. A filter that reduces wavelengths above 570 nm to below-ambient levels may allow ambient or above-ambient amounts of light of one or more wavelengths from 490 nm to 570 nm or from 520 nm to 570 nm to pass therethrough. In some embodiments, visible light having wavelengths below 520 nm may also be filtered, and may restrict ocular light therapy to ambient or above-ambient amounts of one or more wavelengths of 520 nm to 570 nm. Non-limiting examples of such a filter include those available from LEE Filters of Hampshire, UK; those available from GAM Products, Inc. of Los Angeles, California; and those available from Cotech Sensitising Ltd. of Tedegra, Gwent, South Wales, UK.

Although the foregoing description contains many specifics, these should not be construed as limiting the scope of the invention or of any of the appended claims, but merely as providing information pertinent to some specific embodiments that may fall within the scope of one or more of the appended claims. Other embodiments of the invention may also be devised which lie within the scope of one or more of the appended claims. The scope of each claim is, therefore, limited only by the language recited therein and the legal equivalents to the elements recited thereby. All combinations, additions, deletions and modifications, as disclosed herein, that fall within the meaning and scopes of the claims are to be embraced thereby.

What is claimed:

1. A system for administering light therapy, comprising:
a first light source that emits a first peak of visible light in a range of 460 nm to 520 nm; and a second light source that emits a second peak of visible light in a range of above 520 nm to less than 540 nm,
at least one of the first peak of visible light emitted by the first light source and the second peak of visible light emitted by the second light source exceeding an intensity of a corresponding bandwidth in standard indoor lighting at 500 lux.

2. The system of claim 1, wherein the system emits substantially no light outside of a range of 460 nm to 570 nm.

3. The system of claim 2, further comprising:
at least one filter for limiting emission of extraneous wavelengths of visible light from at least one of the first light source and the second light source.

4. The system of claim 3, wherein the at least one filter limits passage of the extraneous wavelengths of visible light through the filter to ambient or below ambient amounts.

5. The system of claim 3, wherein the at least one filter prevents passage of the extraneous wavelengths of visible light through the filter.

6. The system of claim 3, wherein the at least one filter limits an intensity of the extraneous wavelengths of visible light emitted beyond the at least one light source to a subject in such a way that a collective intensity of each peak of the extraneous wavelengths of visible light is less than a collective intensity of the intensity peak of the at least one first bandwidth of visible light.

7. The system of claim 3, wherein at least one of the first light source and the second light source comprises a source of white light.

8. A system for administering light therapy, comprising:
a first light source that emits an above ambient intensity of at least one first bandwidth of visible light including a first intensity peak at a wavelength in a range of 460 nm to 520 nm, the above ambient intensity of the at least one first bandwidth exceeding an intensity of the at least one first bandwidth in standard indoor lighting at 500 lux; and
a second light source that emits an above ambient intensity of at least one second bandwidth of visible light including a second intensity peak at a wavelength in a range of above 520 nm to less than 540 nm, the above ambient intensity of the at least one second bandwidth exceeding an intensity of the at least one second bandwidth in standard indoor lighting at 500 lux.

9. The system of claim 8, wherein the system emits substantially no light in a range of greater than 570 nm to 750 nm.

10. The system of claim 8, further comprising:
at least one filter for limiting emission of extraneous wavelengths of visible light having wavelengths of greater than 570 nm to 750 nm by at least one of the first light source and the second light source.

11. The system of claim 10, wherein the at least one filter limits passage of the extraneous wavelengths of visible light through the filter to ambient or below ambient amounts.

12. The system of claim 10, wherein the at least one filter prevents passage of the extraneous wavelengths of visible light through the filter.

13. The system of claim 10, wherein the at least one filter limits an intensity of the extraneous wavelengths of visible light emitted beyond the at least one of the first light source and the second light source to a subject in such a way that a collective intensity of each peak of the extraneous wavelengths of visible light is less than a collective intensity of the first intensity peak of the at least one first bandwidth of visible light and less than a collective intensity of the second intensity peak of the at least one second bandwidth of visible light.

14. The system of claim 10, wherein at least one of the first light source and the second light source comprises a source of white light.

15. A system for administering light therapy, comprising:

at least one first light source that emits at least one first bandwidth of visible light including a first intensity peak at a wavelength in a range of 460 nm to 520 nm, an intensity of the first intensity peak exceeding an intensity of a corresponding bandwidth in standard indoor lighting at 500 lux, each peak of visible light below 460 nm emitted by the light source, and an intensity of each peak of visible light above 570 nm emitted by the at least one light source; and at least one second light source that emits at least one second bandwidth of visible light including a second intensity peak at a wavelength in a range of above 520 nm to less than 540 nm, an intensity of the second intensity peak exceeding an intensity of a corresponding bandwidth in standard indoor lighting at 500 lux, each peak of visible light below 460 nm emitted by the light source, and an intensity of each peak of visible light above 570 nm emitted by the at least one light source.

16. The system of claim 15, wherein the system does not emit light in a range of above 570 nm to 750 nm.

17. The system of claim 15, further comprising:

at least one filter for limiting emission of extraneous wavelengths of visible light having wavelengths of less than 460 nm and/or greater than 570 nm, by the at least one light source.

18. The system of claim 17, wherein the at least one filter limits passage of the extraneous wavelengths of visible light through the filter to ambient or below ambient amounts.

19. The system of claim 17, wherein the at least one filter prevents passage of the extraneous wavelengths of visible light through the filter.

20. The system of claim 17, wherein the at least one filter limits an intensity of the extraneous wavelengths of visible light emitted beyond the at least one light source to a subject in such a way that a collective intensity of each peak of the extraneous wavelengths of visible light is less than a collective intensity of the first intensity peak of the at least one first bandwidth of visible light and less than a collective intensity of the second intensity peak of the at least one second bandwidth of visible light.

21. The system of claim 17, wherein at least one of the first light source and the second light source comprises a source of white light.

\* \* \* \* \*